(12) United States Patent  
Potyrailo et al.

(10) Patent No.: US 9,389,296 B2  
(45) Date of Patent: Jul. 12, 2016

(54) METHOD FOR SENSOR READER CALIBRATION

(71) Applicant: GENERAL ELECTRIC COMPANY, Schenectady, NY (US)

(72) Inventors: Radislav Alexandrovich Potyrailo, Niskayuna, NY (US); Ian James Forster, Chelmsford (GB)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 476 days.

(21) Appl. No.: 13/838,884

(22) Filed: Mar. 15, 2013

(65) Prior Publication Data

US 2014/0028327 A1 Jan. 30, 2014

Related U.S. Application Data

(63) Continuation-in-part of application No. 13/558,499, filed on Jul. 26, 2012, now Pat. No. 9,195,925.

(51) Int. Cl.
*G01R 35/00* (2006.01)
*G01N 33/00* (2006.01)
*G01N 22/00* (2006.01)
*G01N 27/02* (2006.01)
*G01N 22/04* (2006.01)
*A61B 5/00* (2006.01)

(52) U.S. Cl.
CPC .......... *G01R 35/005* (2013.01); *G01N 33/0006* (2013.01); *G01N 33/0073* (2013.01); *A61B 5/0031* (2013.01); *A61B 2560/0219* (2013.01); *G01N 22/00* (2013.01); *G01N 22/04* (2013.01); *G01N 27/023* (2013.01); *G01N 27/026* (2013.01)

(58) Field of Classification Search
CPC ..... G01N 22/04; G01N 22/00; G01N 27/023; A61B 5/0031; A61B 2560/0219
USPC ......................................................... 324/633
See application file for complete search history.

(56) References Cited

U.S. PATENT DOCUMENTS

| | | | | |
|---|---|---|---|---|
| 4,887,455 A * | 12/1989 | Payne | ................ | G01N 27/126 324/633 |
| 5,831,439 A * | 11/1998 | Suenram | ................ | G01N 22/00 324/633 |
| 6,657,429 B1 * | 12/2003 | Goldfine | ................ | G01B 7/16 324/209 |
| 7,076,858 B2 * | 7/2006 | Eckstein | ............ | G06K 19/0726 257/306 |

(Continued)

*Primary Examiner* — Jermele M Hollington
*Assistant Examiner* — Christopher McAndrew
(74) *Attorney, Agent, or Firm* — Jean K. Testa; Rong Zhang

(57) ABSTRACT

In one embodiment a method for sensor reader calibration comprising: performing a calibration of a sensor reader wherein the calibration comprises open circuit calibration, a short circuit calibration, and a load circuit calibration, or any combination thereof in any succession; enabling connection of a pickup coil to the sensor reader to measure a sensor response; and applying a baseline correction to the sensor response, wherein the baseline correction is obtained utilizing measurements from the calibration step. In a further embodiment, a method for sensor response calibration incorporating environmental correction comprising: measuring a first resonance impedance spectrum of the sensor with a first applied power to the pickup coil; measuring a second resonance impedance spectrum of the sensor with a second applied power to the pickup coil; and applying a correction to the sensor response corresponding to the respective measured first and second resonance impedance spectrum to mitigate for environmental parameters.

20 Claims, 11 Drawing Sheets

(56) References Cited

U.S. PATENT DOCUMENTS

| | | | | |
|---|---|---|---|---|
| 7,168,150 B2* | 1/2007 | Eckstein | G06K 19/0726 | 174/260 |
| 7,449,893 B1* | 11/2008 | Tsironis | G01R 27/32 | 324/623 |
| 7,495,454 B2* | 2/2009 | Rivera | G01N 22/00 | 324/601 |
| 8,933,706 B1* | 1/2015 | Karlquist | G01J 5/04 | 324/633 |
| 8,952,708 B2* | 2/2015 | Nikolenko | G01N 27/028 | 324/633 |
| 2004/0155667 A1* | 8/2004 | Kesil | G01B 7/105 | 324/663 |
| 2008/0191711 A1* | 8/2008 | Rivera | G01N 22/00 | 324/629 |
| 2009/0278685 A1* | 11/2009 | Potyrailo | G06K 7/0095 | 340/572.1 |
| 2010/0295558 A1* | 11/2010 | Eberheim | G01N 27/023 | 324/654 |
| 2011/0068807 A1* | 3/2011 | Kesil | G01N 27/023 | 324/633 |
| 2011/0101996 A1* | 5/2011 | Potyrailo | G01D 21/00 | 324/655 |
| 2011/0156177 A1* | 6/2011 | Merz | G01N 27/4148 | 257/414 |
| 2012/0004851 A1* | 1/2012 | Potyrailo | G01N 33/0073 | 702/19 |
| 2012/0265036 A1* | 10/2012 | Estes | G01N 27/3274 | 600/309 |
| 2012/0265037 A1* | 10/2012 | Bohm | G01N 27/3274 | 600/309 |
| 2012/0289757 A1* | 11/2012 | Boyden | A61N 5/025 | 600/1 |
| 2012/0289758 A1* | 11/2012 | Boyden | A61N 5/025 | 600/1 |
| 2012/0289761 A1* | 11/2012 | Boyden | A61N 5/025 | 600/2 |
| 2013/0060112 A1* | 3/2013 | Pryor | A61B 5/0031 | 600/365 |

* cited by examiner

METHOD FOR SENSOR READER CALIBRATION

CROSS REFERENCE TO RELATED APPLICATION

The present application is a continuation in part (CIP) of U.S. patent application Ser. No. 13/558,499 filed on Jul. 26, 2012.

BACKGROUND

The subject matter disclosed herein relates to chemical and biological sensors, and more particularly, the recalibration of a sensor reader to mitigate for environmental parameters.

Chemical and biological sensors are often employed in a number of applications where the detection of various sensor signals may be used to discern useful information. For instance, measuring the presence of vapors by discerning a change in certain environmental variables within or surrounding a sensor may be particularly useful in monitoring changes in biopharmaceutical products, food or beverages, monitoring industrial areas for chemical or physical hazards, as well as in security applications such as residential home monitoring, homeland security in airports, in different environmental and clinical settings and other public venues wherein detection of certain harmful and/or toxic vapors may be particularly useful.

One technique for sensing such environmental changes is by employing a sensor, such as a radio frequency identification (RFID) sensor, coated with a particular sensing material. Also, sensors may be arranged in an array of individual transducers which are coated with sensing materials. Many sensor arrays include a number of identical sensors. However, while using identical sensors simplifies fabrication of the sensor array, such an array may have limited capabilities for sensing only a single response (e.g. resistance, current, capacitance, work function, mass, optical thickness, light intensity, etc). In such applications, it may be beneficial to include an array of sensors wherein different transducers in the array employ the same or different responses (e.g. resistance, current, capacitance, work function, mass, optical thickness, light intensity, etc.) and are coated with different sensing materials such that more than one property can be measured. Disadvantageously, fabricating a sensor array having individual sensors uniquely fabricated to sense a particular response complicates fabrication of the array.

Further, in practical applications, it is beneficial to use highly selective chemical and biological sensors. That is, it is often desirable to provide a sensor array capable of sensing multiple vapors and vapor mixtures in the presence of other vapors and mixtures. The greater the number of vapors and vapor mixtures that may be present, the more difficult it may be to accurately sense and discern a specific type of vapor or vapor mixture being sensed. This may be particularly true when one or more vapors are present at levels of magnitude greater than the other vapors of interest for detection. For instance, high humidity environments often interfere with the ability of traditional sensors to detect selected vapors. Moreover, variability and inconsistencies exist due to the sensor, environmental parameters, and within the sensor reader itself. A sensor reader is susceptible to environmental parameters, such as temperature.

Therefore, it is beneficial to have a method in which environmental changes such as position changes, noise changes, temperature change, and repositioning changes are accounted for in a multivariate resonance enhanced impedance measurement. Additionally, it may be beneficial to have calibration techniques for the sensor reader itself as an alternative or additional way to mitigate for environmental parameters, such than any inherent inconsistencies and variability of the sensor reader are calibrated for.

Various embodiments disclosed herein may address one or more of the challenges set forth above.

BRIEF DESCRIPTION

A method for sensor reader calibration comprising: performing a calibration of the sensor reader wherein the calibration comprises an open circuit calibration, a short circuit calibration, and a load circuit calibration, or any combination thereof in any succession; enabling connection of a pickup coil to the sensor reader to measure a sensor response, and applying a baseline correction to the sensor response from the pickup coil, wherein the baseline correction is obtained utilizing measurements from the calibration step.

A method for sensor response calibration incorporating environmental correction comprising: measuring a first resonance impedance spectrum of the sensor with a first applied power to the pickup coil; measuring a second resonance impedance spectrum of the sensor with a second applied power to the pickup coil; and applying a correction to the sensor response corresponding to the respective measured first and second resonance impedance spectra to mitigate for environmental parameters.

A method for calibration of a sensor response comprising: measuring a resonance impedance spectrum of sensor in controlled conditions; measuring the resonance impedance spectrum of the sensor proximal to a first material; measuring the resonance impedance spectrum of the sensor proximal to a second material; analyzing the response of the sensor to both the first and second material wherein a multivariable relationship of the sensor response of the first and second material to a controlled condition is established; and applying correction to the measured response of the first material, second material, and the controlled conditions to a store value(s), wherein calibration is utilized to test for sensor freshness.

A method for calibration of a sensor response comprising: measuring a resonance impedance spectrum of the sensor in at least one controlled condition; measuring the resonance impedance spectrum of the sensor proximal to a first material; measuring the resonance impedance spectrum of the sensor proximal to a second material; analyzing the response of the sensor to both the first and second materials; determining a multivariable relationship of the sensor response to the first and second material to the controlled condition; and applying a correction to the measured response of the first material, second material, and the controlled condition to a stored value(s), wherein calibration is utilized to test for sensor freshness.

DRAWINGS

These and other features, aspects, and advantages of the present invention will become better understood when the following detailed description is read with reference to the accompanying drawings in which like characters represent like parts throughout the drawings, wherein.

Figure 3:
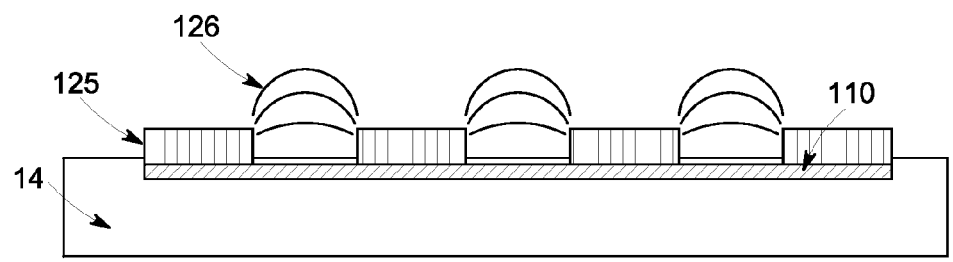
Figure 4:
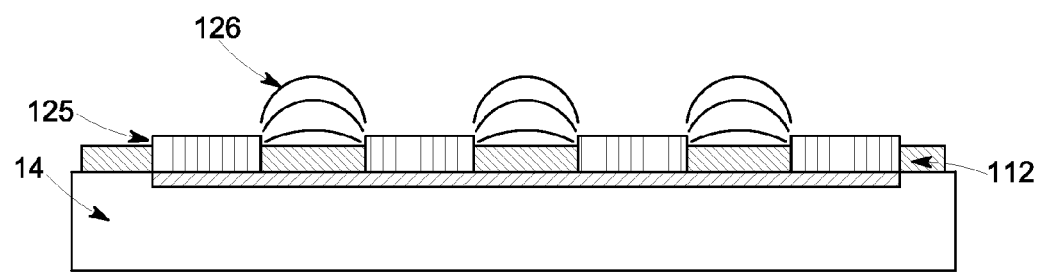
Figure 5:
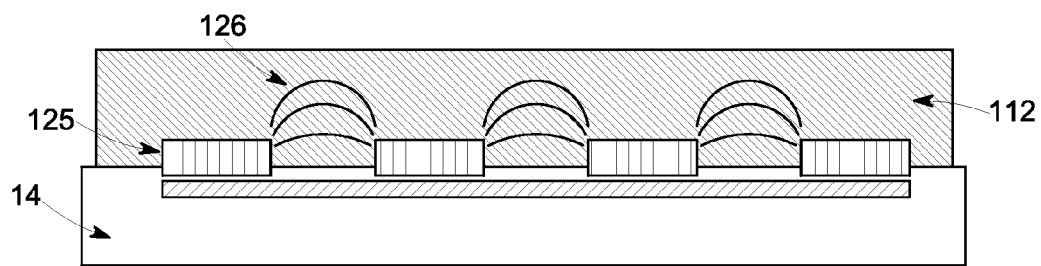

FIGS. 3, 4, and 5 illustrate a sensing system's electrical fields as affected by a sensing material in accordance with embodiments of the invention.

Figure 6:
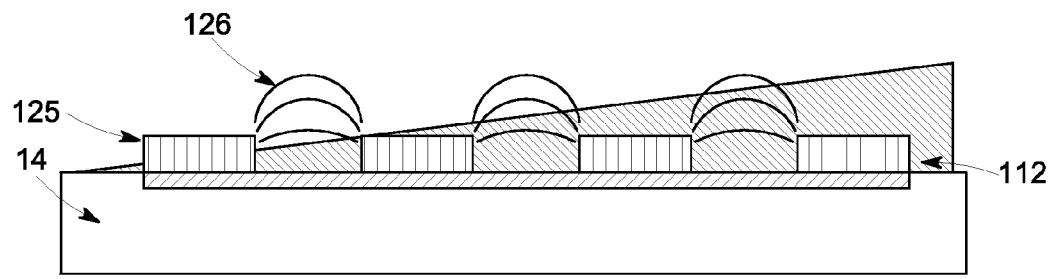

FIG. 6 illustrates a sensing system affected by a gradient sensing film in accordance with embodiments of the invention.

Figure 7:
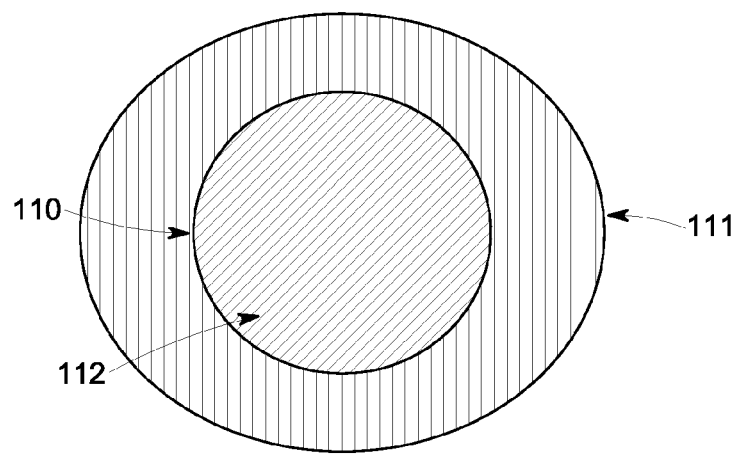

FIG. 7 illustrates a sensing system in which the reference antenna and sensor antenna are concentric in accordance with embodiments of the invention.

Figure 8:
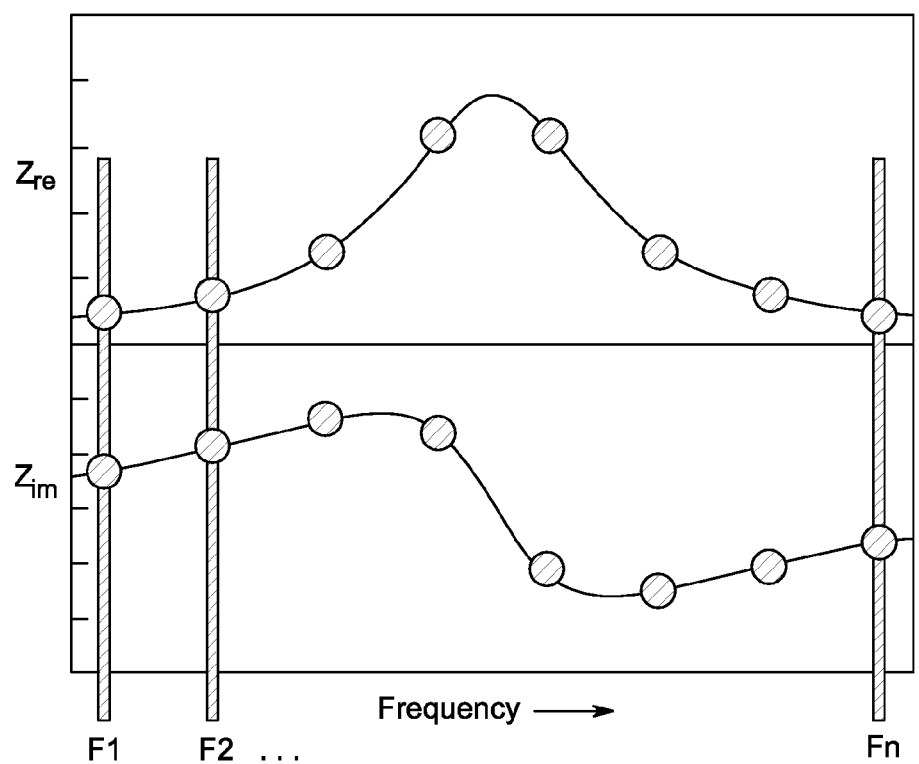

FIG. 8 illustrates the analysis of a resonance response from a sensing system wherein frequencies are measured across such resonance response in accordance with embodiments of the invention.

Figure 9:
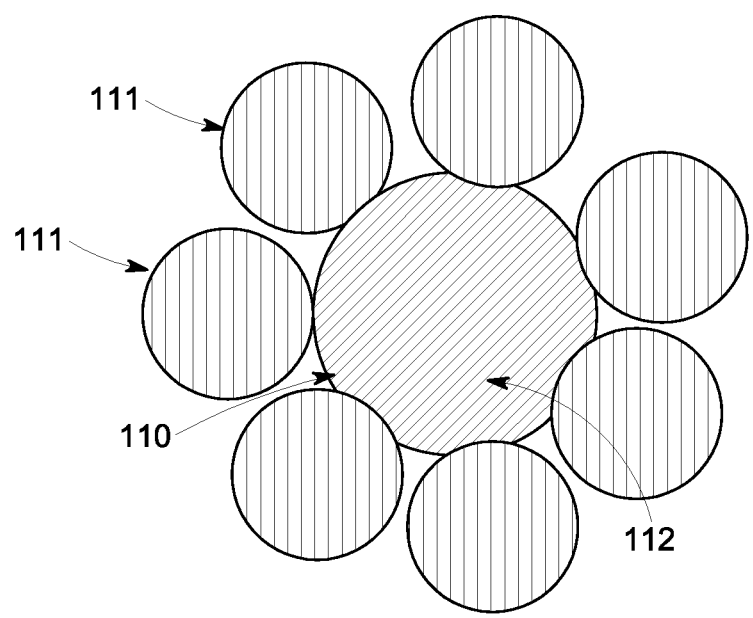

FIG. 9 illustrates a sensing system in which multiple reference antennas and one sensor antenna is used to create a flower petal like structure, in accordance with embodiments of the invention.

FIG. 10 illustrates a sensing system with a reference antenna and sensing antenna located on the same side of the substrate in accordance with embodiments of the invention. 10A shows a side view of the sensing system and 10B shows a cross section view of the sensing system.

FIG. 11 illustrates a sensing system with a reference antenna and sensing antenna located on opposite sides of the substrate in accordance with embodiments of the invention. 11A shows a side view of the sensing system and 11B shows a cross section view of the sensing system.

Figure 12:
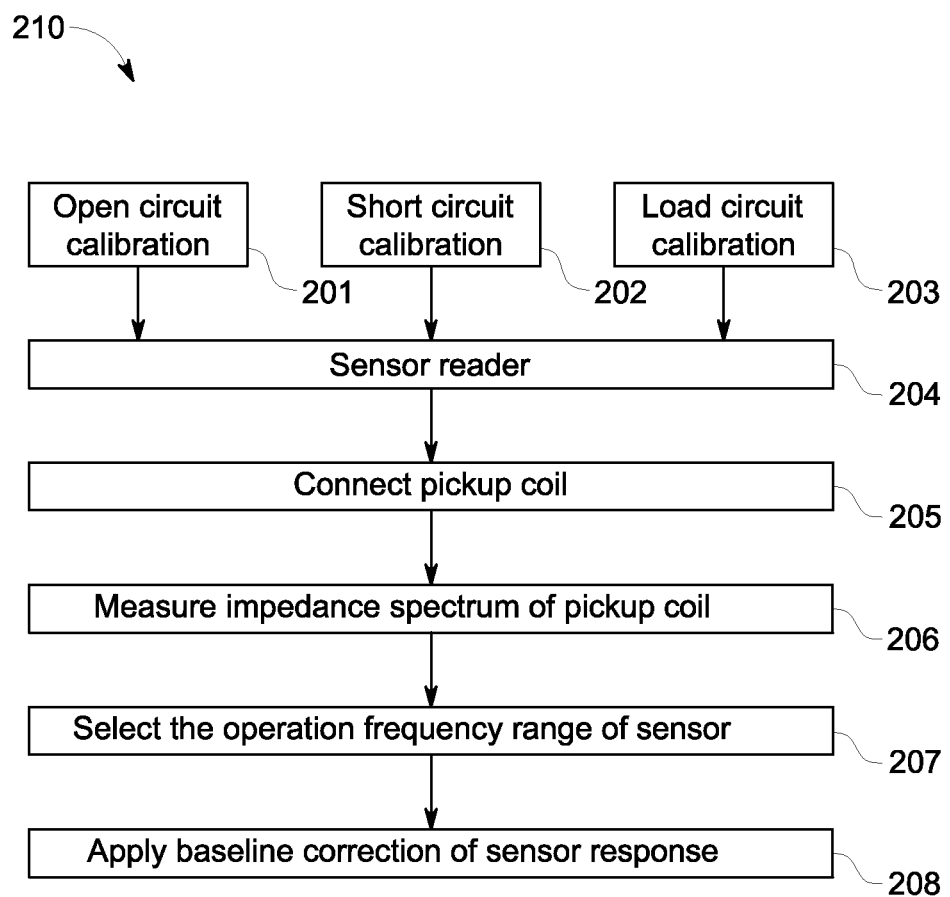

FIG. 12 illustrates a sensor reader calibration via the pickup coil located within the reader, wherein the pickup coil calibrates the reader via a readout of its impedance spectra in accordance with embodiments of the invention.

Figure 13:
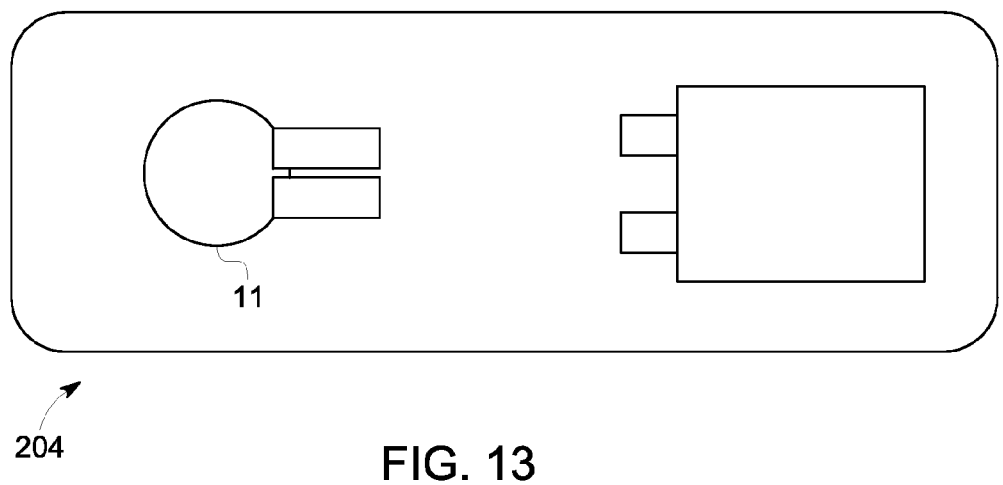

FIG. 13 illustrates a sensor reader, calibration circuit configurations in accordance with embodiments of the invention. 13A shows the elements of open circuit calibration, 13B shows the elements of short circuit calibration, and 13C shows the elements of load circuit calibration.

Figure 14:
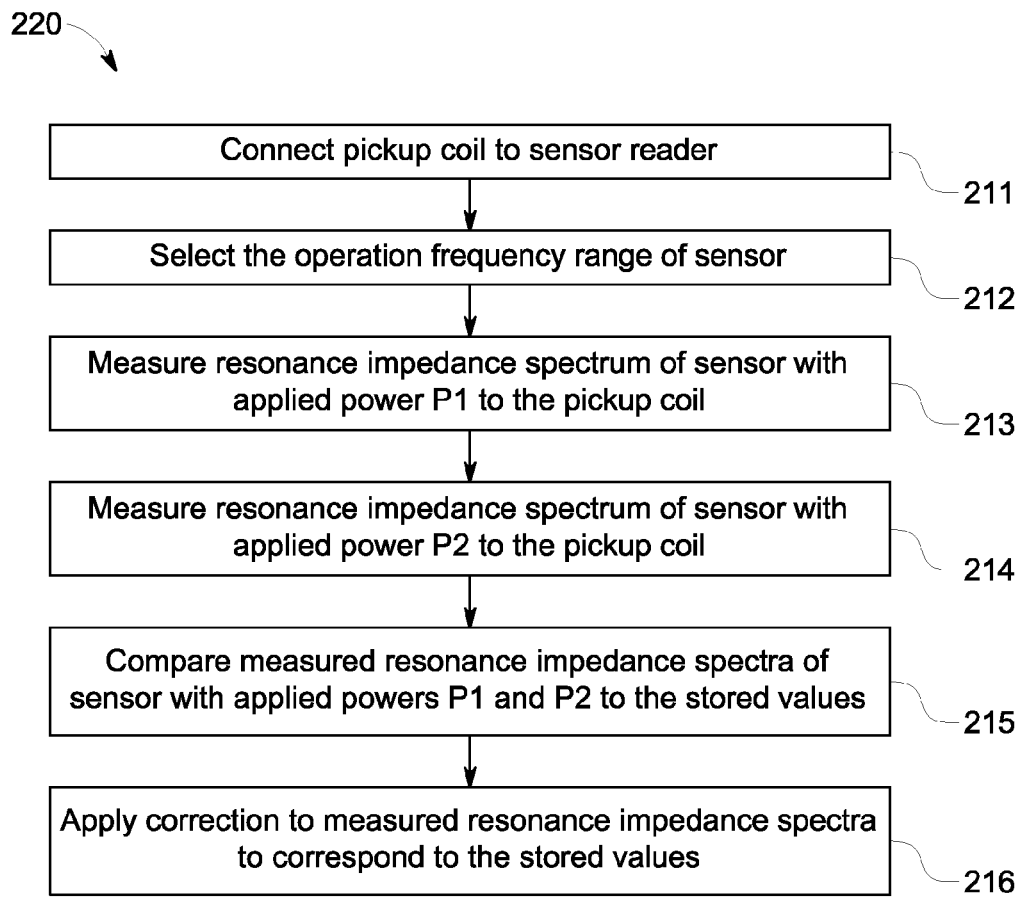

FIG. 14 illustrates a sensor reader calibration performed with an environmental correction utilizing variable power to the reader in accordance with embodiments of the invention.

Figure 15:
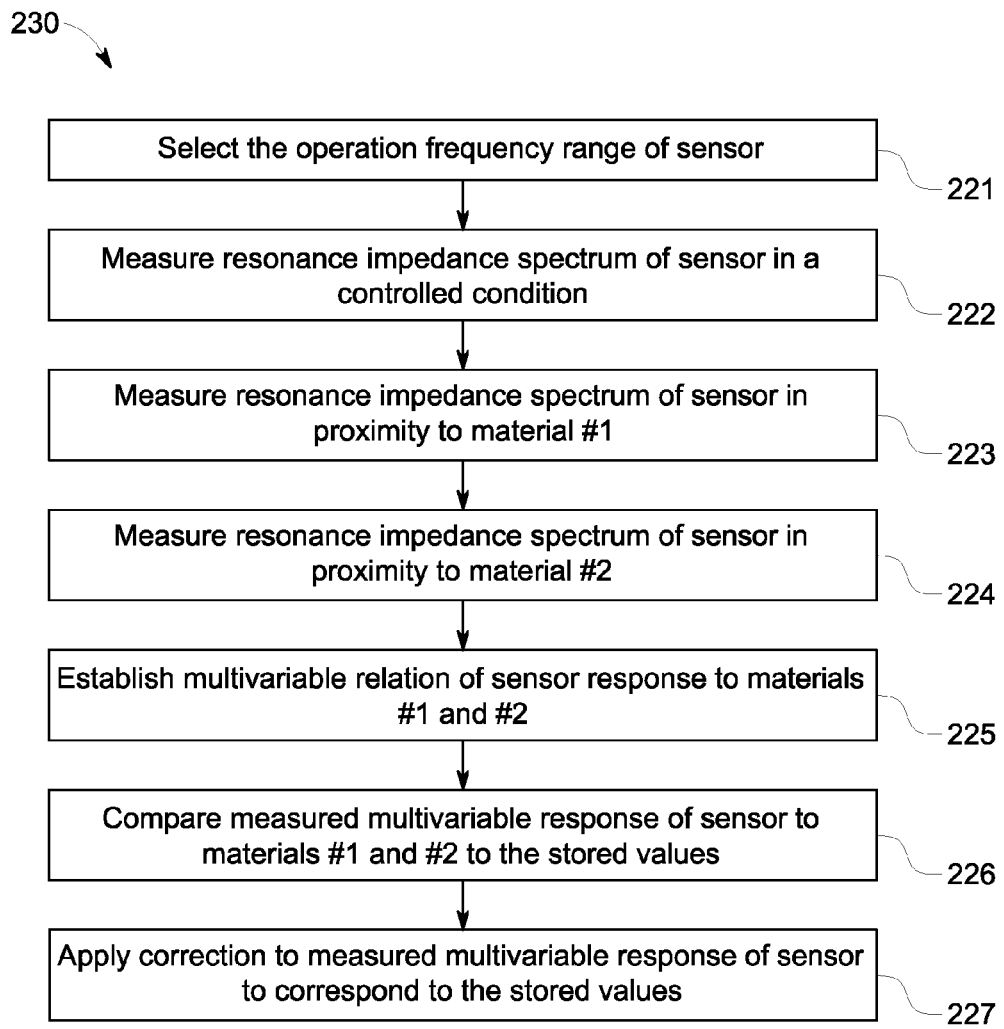

FIG. 15 illustrates the on-site calibration of a sensor by utilizing a sensor reader and known dielectric materials to determine the freshness and condition of the sensor in accordance with embodiments of the invention.

DETAILED DESCRIPTION

Embodiments enclosed herein provide methods for the sensitivity, selectivity, and stability of sensors wherein a sensor is provided and is capable of detecting multiple environmental changes and translating these changes into a resonance enhanced impedance measurement. Non-limiting examples of such multiple environmental changes include individual vapors in their multi-vapor mixtures of a gaseous sample such as air, temperature of the sample and sensor, pressure of ambient air. To accomplish this measurement of multiple environmental changes, a resonant transducer is built and is put in contact with a sensing material.

To more clearly and concisely describe the subject matter of the claims invention the following definitions are provided for specific terms, which are used in the following description and the appended claims.

The term "sensor" and/or "sensing coil" is used to describe a resonant transducer substantially in contact with a sensing material or sensor film. As used herein, the term substantially denotes at least partial coverage.

The term "reference coil" refers to a sensor tag not coated with a sensor material used solely for the purpose of mitigating the effects of position or any present interference. It may also refer to a sensor tag coated with a sensor material that is not exposed to the environment by use of a suitable barrier or a sensor tag coated with a material that makes it preferentially respond to an interference parameter but not to the wanted analyte.

The term "spectral parameters" is used to refer to measurable variables of the sensor response. The sensor response is the impedance spectrum of the resonance sensor circuit of the resonant inductor capacitor resistor (LCR) or RFID sensor. In addition to measuring the impedance spectrum in the form of Z-parameters, S-parameters, and other parameters, the impedance spectrum (both real and imaginary parts) may be analyzed simultaneously using various parameters for analysis, such as, the frequency of the maximum of the real part of the impedance ($F_P$), the magnitude of the real part of the impedance ($Z_P$), the resonant frequency of the imaginary part of the impedance ($F_1$), and the anti-resonant frequency of the imaginary part of the impedance ($F_2$), signal magnitude ($Z_1$) at the resonant frequency of the imaginary part of the impedance ($F_1$), signal magnitude ($Z_2$) at the anti-resonant frequency of the imaginary part of the impedance ($F_2$), and zero-reactance frequency ($F_Z$, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra, are called here "features" or "descriptors". The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

The term "signal" is used to describe measurements of the sensor response. Measurements of the sensor response are performed by measuring spectral parameters such as the full resonance impedance spectrum of the sensor, including its real $Z_{re}$ and imaginary $Z_{im}$ parts of the impedance spectrum. Further, several parameters from the measured $Z_{re}$ and $Z_{im}$ parts of the impedance spectrum can be calculated. Non-limiting examples of these calculated parameters include frequency $F_P$ and magnitude $Z_P$ of maximum of $Z_{re}$, resonant $F_1$ and anti-resonant $F_2$ frequencies of $Z_{im}$, and magnitudes $Z_1$ and $Z_2$ at resonant and anti-resonant frequencies of $Z_{im}$, zero-crossing frequency $F_Z$, and others. Calculated parameters can be also from the measured phase and magnitude of the impedance, and any other parameters typically acquired from a complex impedance measurement. Furthermore, an equivalent circuit of the built sensor can be utilized and the parameters of the equivalent circuit such as circuit resistance, capacitance, and inductance can be calculated from the measured $Z_{re}$ and $Z_{im}$ parts of the impedance spectrum. Depending on the equivalent circuit complexity, more than one resistance, capacitance, and inductance can be calculated in the circuit from the measured $Z_{re}$ and $Z_{im}$ parts of the impedance spectrum. The changes in the measured $Z_{re}$ and $Z_{im}$ parts of the impedance spectrum are induced due to the effects of the multiple environmental changes on the sensing material and transducer components. Non-limiting examples of the transducer components affected by the multiple environmental changes include transducer electrodes antenna, transducer substrate, and transducer memory chip. The transducer may or may not contain a memory chip to store digital information about the RFID tag.

The term "multivariate analysis" refers to a mathematical procedure that is used to analyze more than one variable from the sensor response and to provide the information about the type of at least one environmental parameter from the measured sensor spectral parameters and/or to quantitative information about the level of at least one environmental parameter from the measured sensor parameters. The term "principal components analysis (PCA)" refers to a mathematical procedure that is used to reduce multidimensional data sets to lower dimensions for analysis. Principal component analysis is a part of Eigen analysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

The term "resonance impedance" or "impedance" refers to measured sensor frequency response around the resonance of the sensor from which the sensor "spectral parameters" are extracted.

The term "environmental parameters" is used to refer to measurable environmental variables within or surrounding a manufacturing or monitoring system. The measurable environmental variables comprise at least one of physical, chemical, and biological properties and include, but are not limited to measurement of temperature, pressure, material concentration, conductivity, dielectric property, number of dielectric, metallic, chemical, or biological particles in the proximity or in contact with the sensor, dose of ionizing, radiation, and light intensity.

The term "analyte" is used to describe any chemical substance that is the subject of chemical analysis.

The term "interference" includes any undesired environmental parameter that undesirable affects the accuracy and precision of measurements by the sensor.

As used herein the term "sensing materials and sensing films" includes, but is not limited to, materials deposited onto a transducer's electronics module, such as an RFID sensor, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the RFID sensor, the impedance sensor response changes as a function of pH. Thus, such an RFID sensor works as a pH sensor. When such a polyaniline film is deposited onto the RFID sensor for detection in gas phase, the impedance sensor response also changes upon exposure to basic (for example, $NH_3$) or acidic (for example HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensor material. In order to prevent the material in the sensor film from leaking into the liquid environment, the sensor materials are attached to the sensor surface using standard techniques, such as covalent bonding, electrostatic bonding and other standard techniques known to those of ordinary skill in the art.

As used herein the term "RFID" refers to a data storage and reporting technology that uses radiofrequency electronic tags for storing data and which contains at least two components where the first component is an integrated circuit (IC) memory chip for storing and processing information and modulating and demodulating a radio frequency signal. This memory chip can also be used for other specialized functions, for example it can contain a capacitor. It can also contain at least one input for an analog signal such as resistance input, capacitance input, or inductance input. The second component is an antenna for receiving and transmitting the radio frequency signal.

The term "RFID sensor" is any RFID tag with an added sensing function as, for example, when an antenna of the RFID tag also performs sensing functions by changing its impedance parameters as a function of environmental changes. The accurate determinations of environmental changes with such RFID sensors are performed by analysis of resonance impedance. For example, RFID tags may be converted into RFID sensors by coating the RFID tag with a sensing film. By coating the RFID sensor with a sensing film, the electrical response of the film is translated into simultaneous changes to the complex impedance response, resonance peak position, peak width, peak height and peak symmetry of the impedance response of the sensor antenna, magnitude of the real part of the impedance, resonant frequency of the imaginary part of the impedance, anti-resonant frequency of the imaginary part of the impedance, zero-reactance frequency, phase angle, and magnitude of impedance, and others as described in the definition of the term sensor "spectral parameters". The "RFID sensor" can have an integrated circuit (IC) memory chip attached to antenna or can have no IC memory chip.

The term "writer/reader" includes, but is not limited to, a combination of devices to write and read data into the memory of the memory chip and to read impedance of the antenna. Another term for "writer/reader" is "interrogator".

Figure 1:
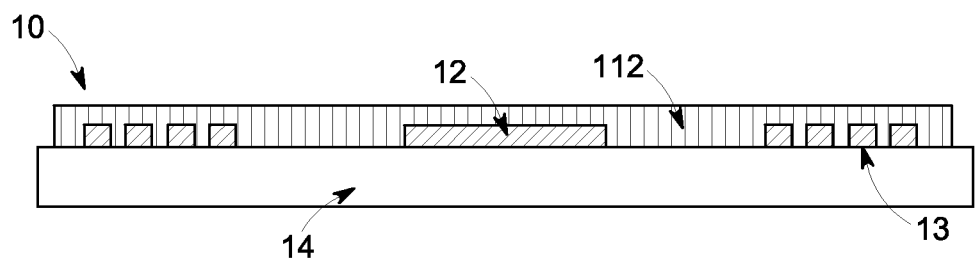
FIG. 1 illustrates a sensing system, in accordance with embodiments of the invention.

Referring to FIG. 1, there is illustrated an RF sensor 10 constructed in accordance with an embodiment of the invention. A sensing material or sensing film 112 is substantially disposed onto an RFID sensor 12 comprised of antenna 13, and a substrate 14, as is well known and established within the art. Antenna 13 is a circuit that includes a resistor element, an inductance element and a capacitor element (not shown) wherein the sensing material affects the capacitance, resistance, and inductance of the antenna by way of changing the signal and sensor response. These changes in the signal and sensor response are provided from the dielectric, conductivity, and dimensional changes of the sensing material upon interactions with analytes.

Figure 2:
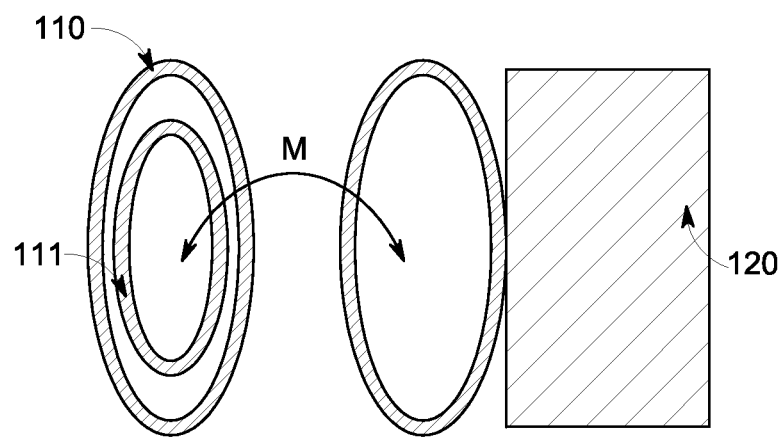
FIG. 2 illustrates a sensing system wherein a reference antenna is used to mitigate for position, in accordance with embodiments of the invention.

Referring to FIG. 2, another embodiment of RF sensor 20 is illustrated in which the mutual inductance coupling M between sensing antenna 110 with reference antenna 111 therein and reader 120. Reference antenna 111 is present to mitigate for positional changes between sensing antenna 110 and the reader 120. The response of any sensing antenna 110 is a combination of positioning and sensing material or sensing film 112 responses; however, as a result of reference antenna's 111 correction and subsequent multivariate analysis, the sensor response predominately displays appropriate resonance impedance allowing for extraction of desired spectral parameters. In order to correct for positioning, the relative ratio of distance between the reference antenna 111 and sensing antenna 110 should be constant such that the measured response is dependent on mutual inductance coupling. In the event a change in position between reference antenna 111 and reader 120 occurs the mutual inductance coupling is altered and reference antenna 111 response is affected; thereby mitigating the positional effects the reader has on the sensing antenna 110.

Referring further to FIG. 2, reference antenna 111, in addition to providing for positional correction, also corrects for environmental parameters. In an embodiment, reference antenna 111 has no sensing material or sensing film disposed upon it thereby tracking only environmental parameters and, by using a multivariate analysis, allows the sensing antenna 110 substantially coated with sensing material or sensing film 112 to track for the specific analyte(s) desired. Multiple sensing materials or sensing films can be used simultaneously to test for multiple desired analytes. A non-limiting example of an environmental parameter that is corrected for by the use of reference antenna 111 is uncontrolled ambient temperature of the environment wherein the sensor is positioned.

Referring to FIG. 3 there is illustrated an embodiment of a RF sensor 30 wherein there is a substrate 14 upon which a sensing antenna 110 is placed. The electrodes of the sensing antenna 125 are displayed so as to illustrate the electric field lines 126 showing field decay as a function of distance from the substrate 14.

Referring to FIG. 4, another embodiment of a RF sensor 40 is shown wherein the thickness of sensing material or sensing film 112 can be uniformly thin, with a range of 0.01 nm to 50 nm, wherein the electric field has the ability to penetrate through sensing material or sensing film 112 into the sample. Similarly, referring to FIG. 5, another embodiment of RF sensor 50 is shown wherein the thickness of sensing material or sensing film 112 can be uniformly thick, with a range of 50 nm to 10,000 nm, wherein the electric field does not appreciably penetrate through sensing material or sensing film 112 into the sample. The thickness of the sensing material or sensing film is adjusted from thin to thick (0.01 nm to 10,000 nm) so as to adjust the response for certain desired analytes and/or to pickup desired concentrations. The control of film thickness gives the ability to adjust selectivity of analyte measurements: using a thin coating provides the ability to measure different analytes with similar response intensity, whereas using a thick coating provides the ability to measure different analytes with enhanced selectivity.

Referring to FIG. 6 there is illustrated another embodiment of RF sensor 60 in which a gradient sensing material or film 112 is used to provide a variable response based on the thickness of the gradient sensing material or sensing film 112. As described below, gradient sensing material or film 112 means a thickness that varies across the length of the sensor from a range of 0.01 nm to ten times to 100 times the distance between the sensing electrodes. For example, if the distance between the electrodes is 10 micrometers, the film thickness will vary from 0.01 nanometers to 1000 micrometers. To account for and accommodate for environmental parameters a constant (see FIG. 4 and FIG. 5) or gradient sensing material or film 112 is disposed onto the sensing coil 110.

The advantage of gradient film sensing material 113, with a range of 0.01 to 100 times the distance between the electrodes, provides a selective variable response based upon the thickness of the gradient film sensing material which varies non-uniformly across the length of the sensor from thin to thick. As shown in FIGS. 4, and 5 there is a distribution of electric fields between the electrodes of sensing coil 110. If the sensing film is relatively thin the selectivity of the sensor will be different from the relatively thick film; however, having a gradient in which the film goes from relatively thick to relatively thin allows for a selective variable response and achieves diversity in the sensor response due to the depth variation in the electromagnetic field penetration. Referring further to FIG. 6, when sensing material or sensing film 112 is thinner than the gap between neighboring electrodes onto which sensing material or sensing film 112 is disposed upon or the electric field penetration depth, then electric field lines 126 probe not only the sensing film but the space above the sensing material or sensing film 112. Similarly, when the thickness of sensing film is bigger than the above mentioned gap or electric field penetration depth then electric field lines 126 predominately probe sensing material or sensing film 112 and not the space above sensing material or sensing film 112. Probing inside or outside sensing material or sensing film 112 allows for greater control and selectivity of the response(s) obtained from sensing film or sensing material 112. A simple combination of a thin sensing material or sensing film and thick sensing material and sensing film provide only two extreme situations of the sensor response and a more limited selectivity of response(s). Using a gradient film thickness over the large total area of electrodes of the sensing coil 125 provides for a larger range of spectral parameters for sensing material or sensing film 112.

Referring to FIG. 7, in another embodiment, sensing antenna(s) 110 and reference antenna(s) can be made into concentric coils with differing operational frequency to provide corrections for environmental and positioning effects. Differing operational frequencies between sensing antenna 110 and reference antenna 111 creates varying resonance impedance thereby optimizing spectral parameters. Sensing antenna 110 and reference antenna 111 operate at different frequencies ranging from 125 kHz to about 1,000,000 GHz. At relatively high frequencies, the sensing and reference antennas have only a small number of coil turns and even one turn or even less than one turn. In these situations, they can be called rings or open rings. The form of the rings can be round or with straight edges and squared corners.

Referring to FIG. 8 there is illustrated an aspect of data interpretation, wherein various frequency ranges (F1 . . . Fn) are examined along various points of the resonant impedance spectra comprised of both real ($Z_{re}$) and imaginary ($Z_{im}$) parts. Both the sensor antenna's and the reference antenna's respective resonant impedance spectra frequency ranges are shown as broken down into a minimum of 8 ranges but may be broken down into 16 ranges, 32 ranges, or any range that is a multiple of 2 greater than 8. As one skilled in the art would appreciate, a greater number of frequency ranges, though causing a slower scan time, creates a better detection resolution and a higher quality of data. Because only the sensing antenna has sensing material and/or film disposed thereon, the resonant impedance spectra of the reference antenna can be used to mitigate for positional effects as well as environmental parameters when compared to the resonant impedance spectra response of the reference antenna(s). In one non-limiting example, the resonance responses of the sensor antenna and reference antenna are measured from about 10 MHz to about 15 MHz. The measured total range of 5 MHz is divided by 8 frequency ranges, thus performing measurements every 625 kHz from 10 to 15 MHz and generating 8 data points across the measured resonance spectrum from 10 MHz to 15 MHz. These 8 data points define the resonant impedance spectrum. In one embodiment, a function may be applied to fit the resonance portion of the scan. In a further embodiment, the function may be applied to a conventional fit algorithm wherein some portion of the spectra is used to deduce desired data. For example, the resonance portion of the scan may comprise 35 percent of the total data points in the scan. Peak positions and magnitude of the peaks may be extracted using a fit function. Non-limiting examples of functions include polynomial fits and centroid fits. The use of function to fit the resonance portion of the scan provides the enhancement of detection resolution and reduction of measurement noise.

In a further embodiment, a multiple antenna configuration may be desired to correct for positioning effects. Referring to FIG. 9, there is shown a multiple antenna configuration comprised of a sensing antenna 110 substantially coated with sensing material or film 112 and multiple reference antennas 111 arranged in a "flower petal" formation overlapping with sensing antenna 110, but other overlapping configurations are contemplated, such as a concentric configuration an offset configuration, and a fractal configuration. Overlapping embodiments allow for a reduction in the size of the overall RF sensor as well as the size of sensing antenna 110 and reference antenna 111. For example, if two antennas with a 5 cm diameter are not overlapped the total size of the RF sensor will be approximately 5×10 cm. In contrast, when the antennas are overlapped with a 4 cm overlapping region the total RF sensor size will be approximately 5×6 cm. By way overlapping, the RF sensor can be made in sizes as small as 1 millimeter, 1 micrometer, and even 1 nanometer.

Figure 10A:
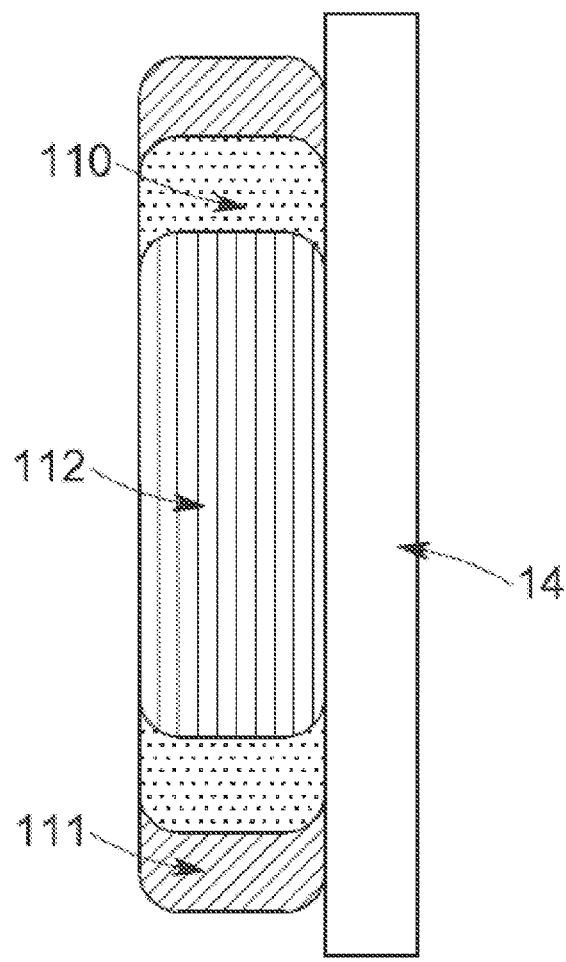
Figure 10B:
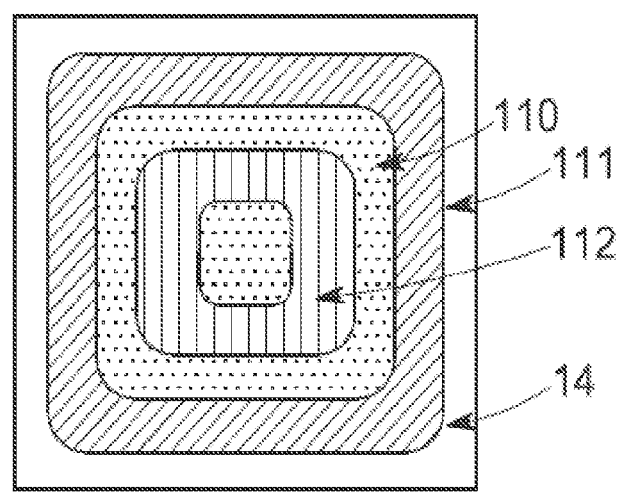

Referring to FIG. 10, a further embodiment of RF sensor is shown wherein sensing antenna 110 with sensing material or film 112 disposed thereon, as well as reference antenna 111 are on the same side of substrate 14. FIG. 10A shows a side view of RF Sensor 20 in which it can be seen that sensing antenna 110 with sensing material or film 112 disposed thereon is on the same side of substrate 14 as reference antenna 111. Further, FIG. 10B shows a cross section view of RF sensor 20 in which it is more clearly seen that sensing antenna 110 and reference antenna 111 are on the same side of substrate 14. Such configuration allows for the mitigation of and compensation for positional effects. As measurements are performed, positional effects are the same for both reference antenna 111 and sensing antenna 110 thereby allowing for a correction in sensing antenna 110 response to only show desired changes.

Figure 11A:
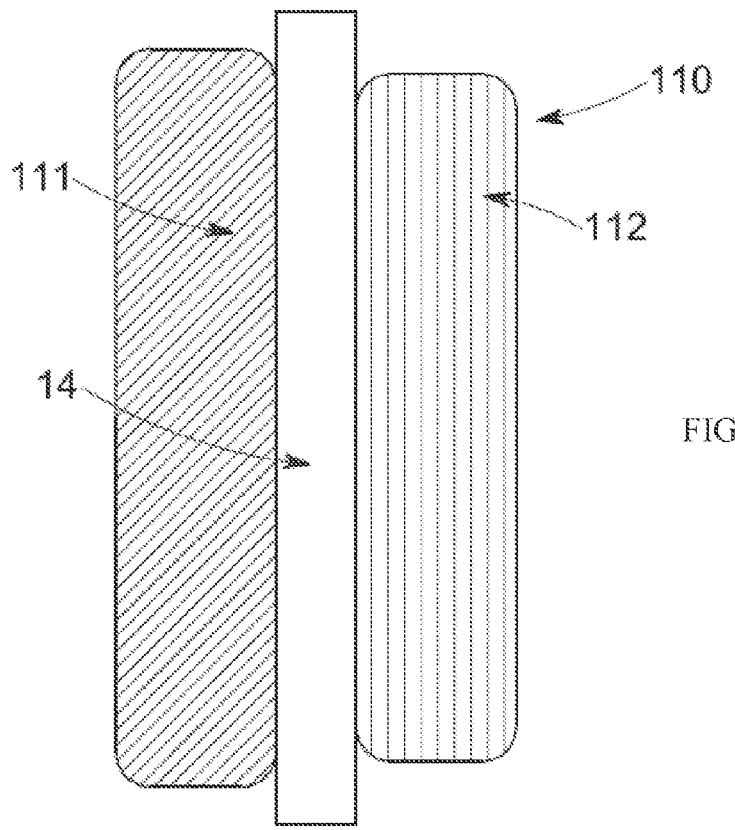
Figure 11B:
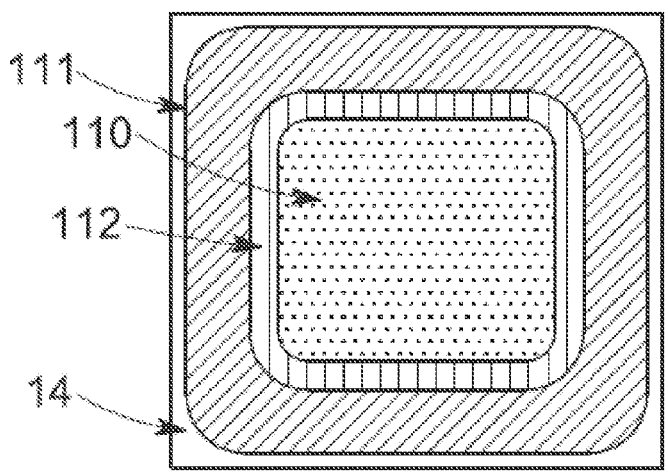

Referring to FIG. 11, a further embodiment is shown wherein sensing antenna 110 with sensing material or film 112 disposed thereon is located on an opposing side of substrate 14 from reference antenna 111. FIG. 11A, shows a side view of RF Sensor 20 in which it can be seen that sensing antenna 110 with sensing material or film 112 disposed thereon is on an opposite side of substrate 14 than reference antenna 111. Further, FIG. 11B shows a cross section view of RF sensor 20 in which it is more clearly seen that sensing antenna 110 and reference antenna 111 are on opposing sides of substrate 14. Such configuration allows for the mitigation of and compensation for environmental parameters. As measurements are taken, sensing antenna 110 accounts for environmental parameters, whereas reference antenna 111, shielded by substrate 14, does not reflect any environmental parameters, thereby allowing for a correction for such environmental parameter.

Referring once again to FIGS. 10 and 11, a further embodiment of a RF sensor is shown wherein a method for sensing analytes employing a RF sensor wherein the RF sensor is comprised of a sensing antenna 110, reference antenna 111, substrate 14, and said RF sensor configured to test for a specific analyte by measurements of the resonant impedance spectra of the sensing and reference antennas at multiple frequencies and the subsequent multivariate analysis of the signal response. The method includes measurements of at least four spectral parameters from both the sensing and reference antennas, selection of at least two of the spectral parameters of the reference antenna response, determination of a correction coefficient of the spectral parameters for the sensing antenna based upon the reference antenna response, and performing a multivariate analysis of corrected spectral parameters for the sensing antenna.

Referring to FIG. 12, an embodiment for a method of sensor reader calibration is shown wherein measurements are taken within the sensor reader 204 so as to calibrate the sensor reader's response in order to mitigate for any inconsistencies and variability within the sensor reader independent of and prior to the electrical connection of the pickup coil. The method of sensor reader calibration comprises performing calibration of the sensor reader using open circuit calibration 201, short circuit calibration 202, and load circuit calibration 203, or any combination thereof in any succession, enabling connection of a pickup coil 205 to the sensor reader 204 to measure a sensor response, and applying a baseline correction to the sensor response 208, wherein the baseline correction is obtained utilizing measurements from the calibration step. Calibration is therefore achieved prior to connection of the pickup coil and one skilled in the art could appreciate the functionality of a sensor reader that includes calibration to be performed by a user or to be calibrated automatically upon powering up of a sensor reader. It should be noted that calibration may be done with or without a memory chip (not shown). Subsequent to calibration, the pickup coil is connected 205 and the impedance spectrum of the pickup coil is preferably measured at at least three frequencies across the impedance spectra 206 as is described in more details above. In a further embodiment, an optimal frequency range for the operation of the sensor is selected (207) and a baseline correction for the sensor response is applied (208) at this optimal frequency. The optimal frequency range is the range of the operation of the sensor reader for the particular intended application of the sensor. This optimal frequency range is determined based on selected criteria that include the dynamic range of required measurements with the sensor, sensor sensitivity, sensor quality factor, and sensor resonant frequency in the absence of the measured analyte or environmental parameter of interest. The baseline correction is derived from the above mentioned calibration measurements and is stored in the reader so the appropriate correction is applied to the sensor response. A non-limiting example of applying a baseline correction to a sensor response includes subtraction of the frequency response of the pickup coil over the operative range of the sensor, or any other mathematical operation to remove effects of the pickup coil on the sensor response. The baseline correction provides the ability to eliminate the effects of the pickup coil resonance on the response of the sensor. The elimination of these effects improves the precision of the sensor measurements. In a non-limiting example, each of the circuit calibrations are performed in sequence.

Figure 13A:
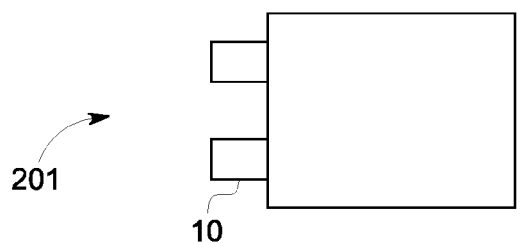
Figure 13B:
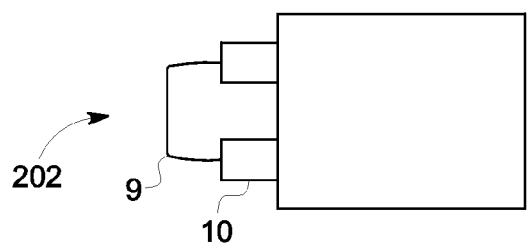
Figure 13C:
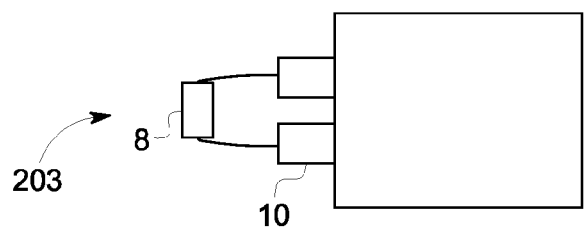

Referring to FIG. 13, there is shown the various circuit calibration configurations within a sensor reader 204 that may be employed as part of the sensor reader calibration. Such calibration includes: open circuit calibration 201, short circuit calibration 202, and load circuit calibration 203. It is contemplated that each of the circuit calibration configurations would reside within the sensor reader and the various configurations may be enabled by switching or other known devices. Referring to FIG. 13A, open circuit calibration 201 is obtained by measuring the open circuit wherein the leads 10 from sensor reader are in open position and a measurement is taken across the two open leads. Referring to FIG. 13B, short circuit (202) calibration is obtained by measuring the response of the sensor reader 204 when the leads 10 are connected 11, specifically meaning the leads are shorted thereby establishing a short circuit. Referring to FIG. 13C, load circuit calibration (203) is obtained by measuring the response of the sensor reader 204 with a predetermined broadband resistor 8 or other equivalent load device on the leads thereby establishing a load circuit. The calibration measurements above are performed prior to electrically connecting the reader to the pickup coil 11. Further, each calibration above may be done individually, collectively, or in any combination desired so as to achieve the desired optimal calibration results. For example, a sensor reader may be configured such that in the event temperature is stable, only short circuit calibration may be conducted to achieve optimal calibration results, or a user defined calibration selecting one or more of the above mentioned sensor reader calibration measurements can be utilized as desired. Summarizing, in accordance with embodiments set forth above, the open, short, and load calibrations minimize sensor reader inaccuracies originating from the changes in ambient conditions, for example, ambient temperature. These calibration responses are saved in the memory (not shown) of the sensor reader and are used to remove the errors attributable to the sensor reader. The open circuit calibrates for the performance of the sensor reader when the connections to the reader are open and nothing is connected to the sensor reader. The short circuit calibrates for the performance of the sensor reader when the connections to the reader are shortened that allows a current to travel along a shortest path where there is essentially no electrical impedance is encountered. The load circuit calibrates for the performance of the sensor reader when a broadband load resistor is attached across the connections to the reader which allows recording of the impedance response of the sensor reader with the attached broadband load resistor.

Referring now to FIG. 14, in a further embodiment, a method of calibration of the sensor reader 220 is performed with an environmental correction comprising use of variable power of the reader. Sensor calibration incorporating environmental correction and mitigating for environmental parameters comprises measuring a first resonance impedance spectrum of the sensor with a first applied power, measuring a second resonance impedance spectrum of the sensor with a second applied power to the pickup coil, and applying a correction to the sensor response corresponding to the respective measured first and second resonance impedance spectrum. Moreover, applying correction to the above mentioned resonance impedance spectrum corresponds to a stored value corresponding to the first and second applied powers used to determine the initial response during a calibration. For example, a sensor tag calibration can be performed with a temperature correction wherein the temperature correction is achieved via variable power.

Referring further to FIG. 14, the method for calibration of the sensor reader 220 incorporating environmental correction comprising the use of variable power of the reader utilized to read the sensor is illustrated. According to this method, the pickup coil is connected to the sensor reader 211, the operational frequency range of the sensor is selected 212, the resonance impedance spectrum of the sensor is measured with a first applied power (P1) to the pickup coil 213, the resonance impedance spectrum of the sensor is measured with a second applied power (P2) to the pickup coil 214, and the respective measured resonance impedance spectra of the sensor at the applied powers of P1 and P2 are compared to the stored values of reference responses of the sensor with powers P1 and P2 215. The stored values of the reference responses of the sensor with powers P1 and P2 are provided from reference measurements of the sensor with these power levels during the sensor calibration. These reference responses of the sensor may be stored in the memory of the sensor reader or within the sensor itself. The reference response of the sensor with powers P1 and P2 determine the initial sensor response during its calibration. The responses after that the initial reference measurements with powers P1 and P2 are typically not expected to substantially deviate from the reference response of the sensor because of the substantially stable sensor performance. If the sensor responses are found to deviate over time, as determined from the comparison of measurements obtained in step 215, then subsequently, correction is applied to the measured resonance impedance spectra to correspond to the stored values (step 216). In embodiments, an IC chip (not shown) is included within the sensor for the purpose of providing different resonant spectra with powers P1 and P2. The differing power levels of P1 and P2, and any other applied power levels utilized, are selected to operate the IC chip (not shown) of the sensor in silent mode (cloaking mode-chip off) and other modes where the chip is either fully or partially operating. The chip is operated in silent mode when the power of the sensor reader is selected to be below a threshold of the needed voltage for the chip to operate. When the chip is fully or partially "on", the sensor response is provided from both the circuitry of the sensor and the response of the sensing film which is a part of the sensor circuit and the chip. Non-limiting examples of the range of operating voltages for a chip include from 2.9 to 3.5V or from 3.0 to 3.4V. Non-limiting examples of the range of required voltages for a chip to be in the intermediate mode include from 2 to 3 V or from 1.5 to 2.5 V. A non-limiting example of optimal frequency range for the operation of the sensor can be from 5 MHz to 20 MHz where the sensor is fabricated to produce sensing response over this frequency range and to operate the memory chip at 13.56 MHz. Another non-limiting example of optimal frequency range for the operation of the sensor can be from 50 MHz to 100 MHz where the sensor is fabricated to produce a sensor response over this frequency range. A non-limiting example of a predetermined broadband load can be a resistor with a nominal value of 10, 50, 100, 500, or 1,000 ohm.

As a non-limiting example, sensor calibration can be performed with a temperature correction wherein the temperature correction is achieved via variable power applied to a chip. In one mode of operation, the chip is off; therefore the circuit response is measured as affected by temperature. In another mode, the chip is partially on and the circuit response is measured as affected by the temperature, including measuring the effects temperature has on the chip response. The measured resonance impedance spectra of the sensor with different applied powers are compared to the stored values at the same powers at a known temperature followed by a correction of the measured resonance impedance spectra to correspond to the stored values at a known temperature. Correction techniques, for example, include comparing polynomial fit coefficients of the stored and measured responses.

Referring to FIG. 15, in a further embodiment, the freshness and condition 230 of a sensor can be determined by the use of on-site calibration by placing the sensor proximal to materials with known dielectric constants. For purposes of this application, proximal means that the sensor response is measured at the same distance from the materials with known dielectric constants. Calibration to determine the freshness of a sensor is achieved by measuring a resonance impedance spectrum of the sensor in controlled conditions, measuring the resonance impedance spectrum of the sensor proximal to a first material, measuring the resonance impedance spectrum of the sensor proximal to a second material, analyzing the response of the sensor to both the first and second material wherein a multivariable relationship of the sensor response to the first and second material to a controlled condition is established, and applying a correction to the measured response of the first material, second material, and the controlled conditions to a store value(s).

The method for calibration is illustrated in FIG. 15. According to this method, the operational frequency range of the multivariable resonant sensor is selected 221 and the resonance impedance spectrum of the sensor is measured in a controlled condition 222. Next, the resonance impedance spectrum of the sensor is measured while the sensor is positioned in close proximity to a first material 223 and the measurement is repeated while the sensor is positioned in close proximity to a second material 224. The response of the sensor to both the first and second material is then analyzed, and the multivariable relationship of the sensor response to the first and second material, and to the controlled conditions is established 225. The measured multivariable response of the sensor to the first material, the second material, and the controlled condition is then compared to the stored values 226, and correction to the measured multivariable response of the sensor is applied to correspond to the stored values 227. Therefore, correction to the measured multivariable response of the sensor is applied to correspond to the stored values. Non-limiting examples of controlled conditions of the sensor are the sensor in air, the sensor in an inert atmosphere such as nitrogen, argon or dry air, the sensor in an atmosphere without the presence of an analyte of interests. Nonlimiting examples of the first and second materials are any materials that have differing values of complex permittivity. Nonlimiting examples of the first and second materials are Teflon, polycarbonate, polyurethane, polyisobutylene, ethyl cellulose, polyepichlorihydrin, silicone, cyanopropylmethyl phenylmethyl silicone, dicyanoallyl silicon, $BaTiO_3$, $BaTiSnO_3$, $Cu_3Ti_4O_{12}$, $Ca_2Nb_4O_{12}$ and any combinations thereof.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for calibration of a sensor response, the method comprising:
   calibrating a sensor reader, the sensor reader calibration comprises an open circuit calibration, a short circuit calibration, and a load circuit calibration, or any combination thereof in any succession;
   calibrating a sensor using the sensor reader, wherein the sensor calibrating is configured for environmental correction, the sensor calibration comprising:
   measuring at least two sensor responses of the sensor at at least two applied powers to the sensor reader, wherein each sensor response of the at least two sensor responses corresponds to one of the at least two applied powers; and
   applying a correction to the sensor responses by comparing reference responses of the sensor corresponding to the at least two applied powers to the sensor responses obtained at the measuring step, wherein the correction mitigates for environmental parameter changes affecting the sensor responses.

2. The method of claim 1, wherein the open circuit calibration is obtained by taking a measurement within the sensor reader when leads from the sensor reader are in an open position and the measurement is taken across the open leads prior to electrical connection of a pickup coil of the sensor reader.

3. The method of claim 1, wherein the short circuit calibration is obtained by taking a measurement within the sensor reader when leads from the sensor reader are connected as a short circuit prior to electrical connection of a pickup coil of the sensor reader.

4. The method of claim 1, wherein the load circuit calibration is obtained by taking a measurement within the sensor reader and the measurement is taken across a predetermined broadband resistor connected to leads from the sensor reader prior to electrical connection of a pickup coil of the sensor reader.

5. The method of claim 1, wherein the correction to the sensor responses comprises subtraction of a frequency response of a pickup coil of the sensor reader over an optimal range for the sensor.

6. The method of claim 1, wherein the correction to the sensor responses removes the effects of a pickup coil of the sensor reader on the sensor responses by mathematical correction.

7. The method of claim 1, wherein the sensor reader calibration is configured to minimize inaccuracies of the sensor reader response originating from ambient conditions.

8. The method of claim 1, wherein the sensor calibration further comprises:
   measuring at least two reference responses of the sensor, each reference response corresponds to one of the at least two sensor responses; and
   determining stability of sensor responses over time by comparing each of the at least two sensor responses obtained at the measuring step to the corresponding reference response, wherein each of the at least two sensor responses and the corresponding reference response are measured at one of the at least two applied powers at different times.

9. The method of claim 1, wherein the correction further comprises:
   measuring at least two reference responses of the sensor, each reference response corresponds to one of the at least two sensor responses, wherein each of the at least two sensor responses and the corresponding reference response are measured at one of the at least two applied powers; and
   correcting each of the at least two sensor responses obtained at the measuring step to correspond to value of the corresponding reference response.

10. A method for calibration of a sensor response, the sensor response calibration incorporating environmental correction, the method comprising:
    calibrating a sensor reader, the sensor reader calibration comprises an open circuit calibration, a short circuit calibration, and a load circuit calibration, or any combination thereof in any succession;
    calibrating a sensor using the sensor reader, wherein the sensor calibrating is configured for environmental correction, the sensor calibration comprising:
    measuring a first sensor response of the sensor with a first applied power to the sensor reader;
    measuring a second sensor response of the sensor with a second applied power to the sensor reader; and
    applying a correction to the sensor responses by comparing reference responses of the sensor corresponding to the first and second applied power to the sensor responses obtained at the measuring step, wherein the correction mitigates for environmental parameter changes affecting the sensor responses.

11. The method of claim 10, wherein the correction further comprises:
    measuring a first and a second reference response of the sensor, each reference response corresponds to one of the at least two sensor responses, wherein each of the at least two sensor responses and the corresponding reference response are measured at one of the at least two applied power; and
    correcting each of the at least two sensor responses obtained at the measuring step to correspond to value of the corresponding reference response.

12. The method of claim 10, wherein the sensor is attached to an integrated circuit chip.

13. The method of claim 12, wherein one of the first and second applied power is utilized to operate the integrated circuit chip in at least one of a silent mode and other modes wherein the integrated circuit chip is either fully or partially operating.

14. The method of claim 12, wherein the integrated circuit chip is switched on or off based on the presence of a threshold environmental parameter(s) so as to calibrate the sensor response to mitigate for such environmental parameter(s) changes affecting the sensor responses.

15. The method of claim 10, wherein the correction further comprises comparing polynomial fit coefficients to the sensor responses and values of the corresponding reference responses of the sensor.

16. A method for calibration of a sensor response, the method comprising:
    calibrating a sensor reader, the sensor reader calibration comprises an open circuit calibration, a short circuit calibration, and a load circuit calibration, or any combination thereof in any succession;
    calibrating a sensor using the sensor reader, wherein the sensor calibrating is configured for environmental correction, the sensor calibration comprising:
    measuring a sensor response in at least one controlled condition;
    measuring a first sensor response proximal to a first material;
    measuring a second sensor response proximal to a second material; and
    applying a correction to the sensor responses by comparing reference responses of the sensor corresponding to the first and the second material to the sensor responses obtained at the measuring step, wherein the correction mitigates for environmental parameter changes affecting the sensor responses.

17. The method of claim 16, wherein the sensor is a multivariable resonant sensor.

18. The method of claim 16, wherein controlled conditions comprises:
    the sensor in air;
    the sensor in an inert atmosphere such as nitrogen, argon, or dry air;
    the sensor in an atmosphere without the presence of an analyte of interest, and any other conditions which result in a known sensor response.

19. The method of claim 16, wherein the first material and second material include any material that has differing values of complex permittivity.

20. The method of claim 16, wherein the first and second materials are selected from at least one of Teflon, polycarbonate, polyurethane, polyisobutylene, ethyl cellulose, polyepichlorihydrin silicone, cyanopropylmethly phenymethyl silicon, dicyanaollyl silicon, $BaTiO_3$, $BaTiSnO_3$, $Cu_3Ti_4O_{12}$, $Ca_2Nb_4O_{12}$, and any combinations thereof.

* * * * *